US006248321B1

(12) United States Patent
Winder et al.

(10) Patent No.: US 6,248,321 B1
(45) Date of Patent: Jun. 19, 2001

(54) ENCAPSULATION OF MICROPARTICLES IN TEARDROP SHAPED POLYMER CAPSULES OF CELLULAR SIZE

(75) Inventors: Richard Scott Winder, Sooke; Jeffery Jerome Wheeler, Surrey, both of (CA)

(73) Assignee: Her Majesty the Queen in right of Canada, as represented by the Minister of Natural Resources, Canadian Forestry Service, Ottawa (CA)

( * ) Notice: Subject to any disclaimer, the term of this patent is extended or adjusted under 35 U.S.C. 154(b) by 0 days.

(21) Appl. No.: 09/229,901

(22) Filed: Jan. 14, 1999

(51) Int. Cl.[7] .......................... A01N 63/04; A01N 25/34; C12N 11/10; C12N 11/04; C12N 5/00

(52) U.S. Cl. ..................... 424/93.5; 424/408; 428/402.2; 435/177; 435/178; 435/182; 435/382

(58) Field of Search .................................... 435/174, 177, 435/178, 180, 182, 382; 424/408, 93.5; 428/402.2

(56) References Cited

U.S. PATENT DOCUMENTS 4,352,883 * 10/1982 Lim ...................................... 435/178
4,409,331 * 10/1983 Lim ...................................... 435/178
4,647,536 * 3/1987 Mosbach et al. .................... 435/177
4,724,147 * 2/1988 Marois et al. ......................... 424/93
5,015,576 * 5/1991 Nilsson et al. .................... 435/70.21
5,786,188 * 7/1998 Lamar et al. ......................... 435/177
5,879,712 * 3/1999 Bomberger et al. ................. 424/489

* cited by examiner

*Primary Examiner*—David M. Naff
(74) *Attorney, Agent, or Firm*—J. Wayne Anderson

(57) ABSTRACT

Microparticles such as propagules of eukaryotic biocontrol agents are encapsulated in cellular-scale polymer capsules that have a diameter similar to normal eukaryotic cells in a range of about 10 $\mu$m to about 400 $\mu$m. The microparticles are encapsulated by adding a hydrophobic dispersion medium such as a mixture of chloroform and hexane or a mixture of corn oil and n-hexadecane having a specific gravity of about 1 and containing an emulsifier such as lecithin to an aqueous suspension of the microparticles and a polymer matrix precursor such as alginate, agitating vigorously to form a stable emulsion of microscopic globules containing a microparticle, and adding the emulsion to an aqueous solution containing a polymerizing agent such as calcium chloride to polymerize and precipitate the globules to form microparticles encapsulated in polymer matrix capsules that may be of a teardrop shape having a length of 40–200% longer than the diameter. Precipitation of the globules is regulated by substantially matching the Specific Gravity of the hydrophobic dispersion medium and the aqueous suspension. The microparticle may be a viable propagule of a weed pathogenic fungus to provide a herbicidal composition.

25 Claims, 10 Drawing Sheets

ENCAPSULATION OF MICROPARTICLES IN TEARDROP SHAPED POLYMER CAPSULES OF CELLULAR SIZE

FIELD OF THE INVENTION

This invention relates to a method for the cellular-scale encapsulation of microparticles, and to microparticles encapsulated according to the method.

BACKGROUND OF THE INVENTION

Recently, there has been considerable interest in encapsulation/immobilization of microparticles, including living cells, propagules of living cells, bacteria, viruses, fungi and the like.

Moreover, it is often desirable to formulate biological control agents so that their propagules are encapsulated and provided with water and nutrients necessary for growth. In this context, the necessity to overcome dew period requirements of weed pathogens is critical. Encapsulation can protect propagules from loss of viability due to desiccation, damage by UV light, and other environmental stresses. It can also aid in packaging inoculum in a form that is easier to manipulate and harder for pests to detect.

Simple and sometimes effective anti-desiccant formulations have spanned the range from oils to polysaccharide gets and guns, etc. There are a raft of papers on the subject, please see Auld & Morin, 1995[1] and Green et al. (1998)[2] for comprehensive overviews. There are various polymer encapsulation methods that have been derived for bacteria and other small targets. In biological control research, most attempts to encapsulate spores and other cells have involved their inclusion in various kinds of macroscopic polymer granules (alginates, pastas), e.g. see Connick et al., 1991[3]. In biological control of weeds, invert emulsions are used with increasing frequency, because they can overcome the requirement for a dew period, e.g. see Connick et al., 1991[4].

The above methods all have limitations. Simple antidessicant gels, etc. have had limited success owing to the high viscosity needed to achieve adequate water-holding properties. In other words, such formulations cannot be easily sprayed, and require far more material than is economically feasible to apply. Invert emulsions suffer similar problems, in that they are bulky, and costly in terms of the amount of material that must be applied. They can cause collateral damage because they can be phytotoxic in their own right, and they require special equipment for application due to their high viscosity. In addition, invert emulsions must be prepared shortly before application, and do not allow for freeze-drying or other types of long term storage. Regarding dry formulations, macroscopic granules containing eukaryotic cells cannot be reduced to a microscopic size without crushing and killing cells. This is unfortunate, because macroscopic granules cannot be easily sprayed and they do not efficiently distribute inoculum or other materials because of their relatively low surface area to volume ratio. Vapor coating methods are also impractical in our experience, due to the cost of the method, the cumbersome equipment required, the exposure of cells to relatively high heat during some coating methods, the dry, piecemeal nature of coatings produced at lower heats, and the larger size of the particles produced. A method is needed to make formulations a more intrinsic part of cells, hence encapsulation.

Currently applicable encapsulation or immobilization techniques tend to produce polyacrylamide or alginate beads in the range of 0.5–1 mm in diameter, too large to be of practical use for cellular-scale applications. They tend to be expensive or unwieldy and rely on methods, equipment, or chemicals that are fairly specialized. It is possible to place aqueous droplets containing acrylamides or other monomers into dispersion media composed of hydrophobic solvents or oils, wherein the drops are held in place as spheres while the monomers polymerize. This method comes closest to our approach, e.g. see Nilsson et al., 1983[5], also see U.S. Pat. No. 4,647,536, but the technique is unwieldy, mostly because the polymerization is proceeding as the drops are forming globules in the solvent.

A major advantage of the present methodology is that we avoid the complicated prior art procedures to extract the capsules from dispersion media, i.e. the capsules form on their way out of the dispersion medium, killing two birds with one stone. This is not only a unique method, but also results in a unique characteristic—the capsules are not encumbered by any significant (visible in the compound microscope) oil coating. There are occasionally some small oil droplets that can be seen in and outside the capsules, but these are a very small portion of the overall material that is produced. Freeing the capsules from the dispersion medium in this manner is desirable for a number of reasons. First, materials with an oily consistency may be difficult to manipulate, concentrate, or formulate for practical applications. Second, the presence of significant amounts of the dispersion medium may affect the performance or behavior of the encapsulated material. Third, the presence of an extra component could complicate legal registration or other types of regulatory approval necessary for commercialization of products. Fourth, on larger scales, aqueous solutions are cheaper than oil solutions. There is another advantage to polymerizing upon exit from the dispersion medium: while Nilsson's stirring method avoids adhesion or bonding (perhaps even fusion) of capsules polymerizing inside the dispersion medium, our method does not require such fine control over agitation, and is thus more reliable and easier to reproduce, particularly if the method is to be scaled-up in volume.

SUMMARY OF THE INVENTION

It is an object of the present invention to encapsulate microparticles e.g. propagules of eukaryotic biocontrol agents with cellular-scale polymer capsules, via a novel, inexpensive method that encapsulates with as much as 100% efficiency.

According to one aspect of the invention, a method is provided for cellular-scale encapsulation of microparticles, comprising:

(i) providing an aqueous suspension of the microparticles and a polymer precursor, the polymer being biodegradable and not requiring heat or pressure to form, (ii) adding a non-cytotoxic, hydrophobic dispersion medium containing an emulsifier, to form an aqueous dispersion, (iii) agitating vigorously to form a stable emulsion of microscopic globules including a microparticle and the polymer precursor, and (iv) adding the suspension to an aqueous solution containing a polymerization agent/catalyst, to polymerize and precipitate the globules and form polymer encapsulated microparticles of cellular scale dimensions.

DESCRIPTION OF THE PREFERRED EMBODIMENTS

Figure 1:
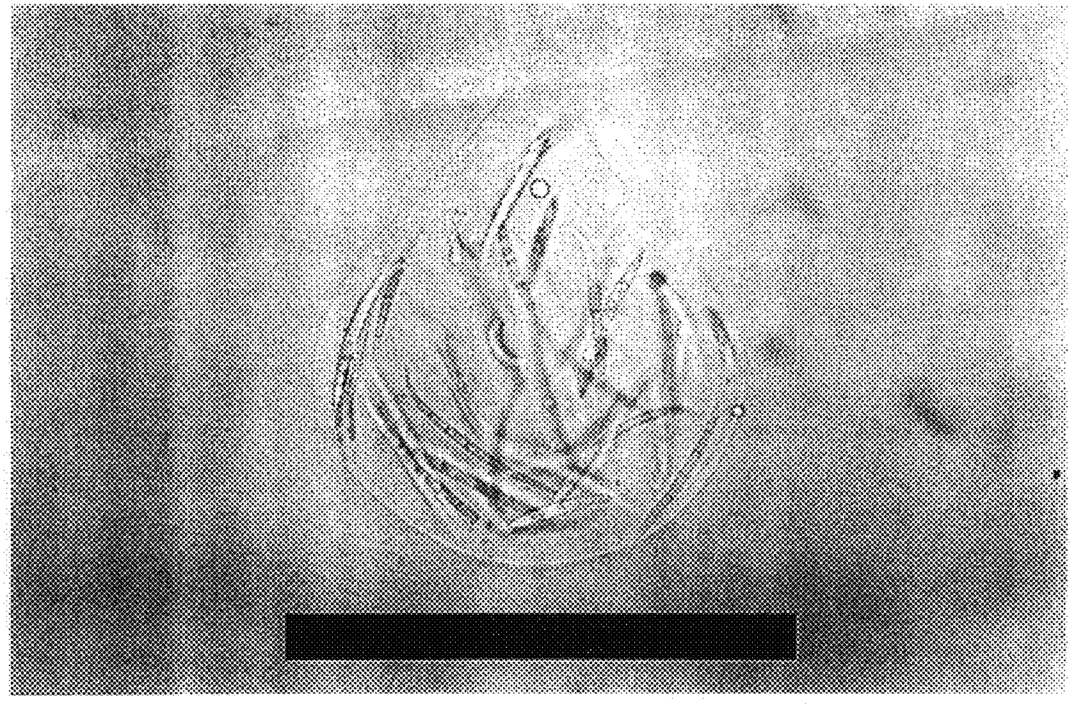
FIG. 1 is a photomicrograph of a capsule containing macroconidia of *Fusarium avenaceum* (Fr.) Sacc., generated via the corn oil method. The black scale bar is 100 μm long.

The method involves the use of stabilized (with a suitable emulsifier) emulsions in conjunction with an aqueous solution containing a polymerizing agent. To form the emulsion, the cells or microparticles to be encapsulated are suspended in aqueous solutions containing polymer precursors, and this is added to a hydrophobic dispersion medium (solvent) containing the emulsifier e.g. lecithin. After vigorous agitation, a stable emulsion of microscopic globules containing the polymer precursor and the material to be encapsulated form within the hydrophobic dispersion medium. To polymerize these globules, the emulsion is layered onto the solution containing the aqueous polymerizing agent and the globules are allowed to precipitate into this solution and polymerize. This method is generally applicable to a wide range of chemical solvents (see below), and is not restricted to the solvents tested in the experiments outlined below. Because it is possible to include air bubbles in emulsions, the dispersion medium need not necessarily be lighter than water, and could, in fact, be located under the catalyst (polymerizing agent) solution as globules rise and polymerize to form buoyant capsules. The method is also applicable to a variety of microparticles and cellular material, including yeast cells, somatic cells and sexual cells. Of particular interest is the encapsulation of viable fungal propagules, useful as biocontrol agents, and synthetic spores.

The key factors are 1) The presence of a stabilized emulsion containing aqueous globules of cellular-scale dimensions; 2) The presence of non-miscible dispersion medium and water phases with low surface tension at their interface; 3) The use of fast-polymerizing materials to encapsulate, and 4) bead (globule) formation before polymerization. For encapsulation of living materials, the use of certain solvents (e.g. n-hexadecane) to adjust globule size and interface surface tension is preferred to preserve cell viability.

Cellular-scale is defined here as a size range similar to the diameter of normal eukaryotic cells, i.e. ranging from approximately 10 μM to approximately 400 μM.

Summary of Alternative Compounds Useful in Encapsulation Technique

A. Encapsulation polymers

TABLE 1

A list of polymers useful in encapsulation technique.

| Polymer | Organism | Reference |
|---|---|---|
| pregelatinized cornstarch | Bacillus thuringiensis | McQuire and Shasha (1990) J. Econ. Entomol. 83:5, 1813–7 |
| Alginate | Bacillus thuringiensis | Vijayan and Balaraman (1995) Southeast Asian J. Trop. Med. Public Health 26:1, 183–7 |
| Alginate | Bacillus thuringiensis | Elcin (1995) J. Microencapsul. 12:5, 515–23 |
| polylactic-coglycolic acid | Protein | Yang and Cleland (1997)J. Pharm. Sci. 86:8, 908–14 |
| alginate-polylysine | None | De Vos, De Haan, Schilfgaarde (1997) Biomaterials 18:3, 273–8 |
| Desaminotyrosinetyrosylhexyl ester with phosgene | None | Ertel Kohn, Zimmerman, Parsons (1995) J. Biomed Mater Res. 29:11, 1337–48 |
| poly(lactic acid-co-glycolic acid) | None | Menei Boisdron-Celle, Croue, Guy, Benoit (1996) Neurosurgery, 39:1, 17–23 |
| derivatized alpha-amino acids | Ovalbumin | Vaccine (1996) 14:8, 785–91 |
| polyacrylonitrile-sodium methallylsulphonate | Hepatocytes | Biomaterials, 1995, 16:10, 753–9 |
| cellulose sulfate, poly(methylene-co-guanidine)hydrochloride | Living cells | Nat. Biothechnol. 1997 15:4, 358–62 |

TABLE 1-continued

A list of polymers useful in encapsulation technique.

| Polymer | Organism | Reference |
|---|---|---|
| agarose/poly-(styrene sulfonic acid) (agarose/PSSa) | PC12 cells | Exp. Neurol. 1996 138:1, 169–75 |
| Methacrylic acid and dimethylaminoethyl methacrylate | Raji Cells | Biomaterials, 1995 16:4, 325–35 |
| water-insoluble hydroxyethyl methacrylate-methyl methacrylate copolymer and polyethylene glycol | PC12 cells | Biomaterials, 1996, 17:3, 267–75 |
| poly(2-hydroxyethyl methacrylate) and poly(2-hydroxyethyl methacrylate-co-methyl methacrylate) | Insulin releasing cells | J. Biomater. Sci. Polym. Ed. 1997, 8:8, 575–86 |
| alginate emulsified in vegetable oil | Bacillus Calmette-Guerin | J. Microencapsul. 1997, 14:5, 627–38 |
| hydroxyethyl methacrylate-methyl methacrylate copolymer (HEMA-MMA) | Erythrocytes | Journal of Biomedical Materials Research 24(9), 1241–1262 |
| sodium alginate, kaolin clay | Cercospora kikuchii | Phytopathology 75(2), 183–185 |
| Calcium alginate | Live cells and enzymes | Journal of Microencapsulation Vol. 12, no. 3, 255–262 |
| Alginate/poly-L-lysine (alg/PLL), nylon or crosslinked polyethyleneimine (PEI) membranes | Lactoccus lactis subsp. cremoris | J. Microencapsulation Vol. 11, no. 2, 189–195 |
| Biodegradable mixtures of pectin and Polyvinyl alcohol | None | http://www.arserrc.gov/TechPectinPVA.htm (U.S. Pat. app. 08/529,299 |
| Alginate-polylysine | Isolated rat hepatocytes | Biomat., Art. Cells & Immob. Biotech. 19(4), 675–686 |
| Agar | | |

Some additional polymers could be incorporated in Table 1. They can be formed and molded without elevated temperature or pressure and could therefore be used to encapsulate cells. Even if they do not polymerize as quickly as alginate, the alginate capsules could be used to hold these other polymers in place until they harden. The general classes of polymers not requiring heat or pressure to form include:

Epoxy plastics
Polyesters
Polyurethanes
Silicone plastics
Acrylamids or polyacrylamides Note that any of the preceding polymers (Table 1 and list) could be combined in mixtures. Note also that the polymer may degrade or solidify with time, or with exposure to light, heat, chemical signals, or environmental signals, thereby affecting the biological or physical performance of the encapsulated material. Other biological polymers have been frequently listed in the literature as adjuvants for biological control agents. Examples of general classes of biological compounds that could be useful alone or in mixtures to create biodegradable polymer capsules for these agents or other materials could include:

Carageenans
Fibrins
Sugars and polysaccharides, including starches
Amino acids and proteins
Glycoproteins and peptidoglycans
Nucleic acids, DNA, and RNA
Fatty acids and lipids
Lipoproteins and liposaccharides
Organic polymers containing mixtures of any of the above compounds B. Emulsifiers Common water-in-oil emulsifiers that could be used for the emulsification technique include:

General groups:
Lecithins
Glycerides (including mono- and di-glycerides)
Polysorbates
Glyceryl esters
Sorbitan esters
Cholesterol and other steroids
Acacia extracts
Gelatins
Phospholipids (bilayer forming)

Specific examples of emulsifying agents from "Remington's Pharmaceutical Sciences" (1990) include:

Sorbitan trioleate
Sorbitan tristearate
Propylene glycol monostearate
Sorbitan sesquioleate
Glycerol monostearate (non self-emulsifying)
Sorbitan monooleate
Propylene glycol monolaurate
Sorbitan monostearate
Glyceryl monostearate (self-emulsifying)
Sorbitan monopalmitate
Sorbitan monolaurate
Polyoxyethylene-4-lauryl ether
Polyethylene glycol 400 monostearate
Polyoxyethylene-4-sorbitan monolaurate
Polyoxyethylene-20-sorbitan monooleate
Polyoxyethylene-20-sorbitan monopailitate
Polyoxyethylene-20-sorbitan monolaurate
Polyoxyethylene-40-stearate
Sodium oleate
Sodium lauryl sulfate Lecithin, bilayer forming lipids and cholesterol are preferred. Lecithin is most preferred.

C. Alternative oils and solvents (dispersion medium)

Almost any naturally occurring biologically derived oil can be used for the oil portion of the dispersion medium, as most will be both hydrophobic and non-toxic to cells. Synthetic oils or petroleum based oils could be useful in encapsulation of non living targets, but most if not all would probably have some toxicity to living cells. It is to be expected that non-toxic synthetic oils that mimic naturally occurring biologically derived oils can be used, but they would probably be more expensive.

Regarding solvents, it would be difficult to find many ordinary types that would not break down cell membranes and kill cells. However, because methylation and other ways of creating chemical derivatives provides an opportunity to design more solvents than we can list in one chart, we will simply describe the characteristics the solvent should have to be useful in the encapsulation approach:

Hydrophobic (hydrocarbons), miscible in oils

Structure (chains, branches, or cyclic rings) arranged so that the specific gravity is relatively close to the specific gravity of water No reactive groups in the molecule that would be toxic to cells (no chlorine, carboxyl, hydroxyl, etc. groups).

Molecules large enough that they don't easily penetrate biological membranes

Relatively non-viscous

METHOD

Note that fungal propagules used throughout these methods were produced using standard microbiological culturing methods, e.g. consult Winder, 1996[6], the disclosure of which is incorporated herein by reference. Also note that the percentage values for all solution concentrations were calculated on a volume:volume basis.

Case 1: Alginate capsules using a Chloroform:Hexane solvent system.

One of the main considerations in the formation of an emulsion is the tendency of the droplets to cream or precipitate. The ideal emulsion is one in which the individual droplets remain individual and neither sink nor float. One means of achieving this is to form the emulsion droplets in a medium with substantially the same specific gravity as the droplets themselves. Rapid mixing, homogenization, sonication, etc. can emulsify water and organic solvent, but the droplets usually rapidly float to the surface (cream) and fuse until eventually one is left with a two-phase system. Emulsifiers such as lecithin slow this process down somewhat. It was found that if one mixed chloroform with the lighter hexane, it resulted in a solvent system which was the same specific gravity as a 0.5% aqueous alginate solution emulsified into it. This required a mixture ratio of 1.5 mL hexane to 0.5 mL chloroform. Vortexing several drops of 1% sodium alginate solution added to 10 mnL of the solvent lead to rapid breakdown of the water phase and separation. When lecithin was included (25 mg to start with, but this can be reduced), it was possible to form small droplets which were very stable. By adjusting the ratio of chloroform to hexane it was possible to completely suspend these droplets, or cause them to sink or cause them to float. In all cases, the droplets did not fuse.

To polymerize the droplets, the organic solvent containing the alginate droplets was layered over a 1 mL solution of 0.1 M calcium chloride ($CaCl_2$) in a test tube (calcium ions cause liquid alginate to immediately polymerize and harden). During the first trial, the $CaCl_2$ contained about 1 μg of A23187 (a calcium ionophore) to enhance penetration into the capsules, but the ionophore was found to be unnecessary in subsequent attempts. The emulsion droplets slowly precipitated from the solvent phase and polymerized upon crossing the solvent/$CaCl_2$ solution interface. These droplets collected on the bottom of the test tube and were recovered with a Pasteur pipette and washed with water to remove any residual solvent.

The resulting capsules were all less than 500 μm in diameter. As seen in FIG. 1, most were uniformly teardrop-shaped, with symmetrical morphology and tails, since the polymerization proceeded quickly. Conidia (spores) of the fungus *Fusarium poae* (Peck) Wollenw. (a potential fungal biocontrol agent for marsh reed grass) were encapsulated into the alginate beads with 100% efficiency. In subsequent trials, it was found that the concentration of alginate (viscosity of the emulsified droplets) affected the size of the beads formed. Lower alginate concentrations caused smaller beads (100 μm or less) to form. Lower alginate concentrations required higher hexane:chloroform ratios to achieve precipitation of the droplets into the $CaCl_2$ phase. The amount of lecithin used in the first experiment (25 mg) was far in excess of what was necessary to achieve a stable emulsion. In subsequent trials, 0.1 mg or less was needed.

At this point, the feasibility of encapsulation using the method was demonstrated. However, the chloroform was probably toxic to the spores, as they did not germinate. For applications involving living cells, the method required adaptation. It was possible to address this, since the feature critical to achieving adequate precipitation of capsules is the regulation of emulsification and interface with the aqueous polymerizing solution, and not the particular solvents used.

Case 2: Corn oil: hexadecane solvent system.

It was found that a stable emulsion could be formed by emulsifying alginate solutions in a dispersion medium of a mixture of corn oil:n-hexadecane containing lecithin. The resulting droplets also polymerized by precipitation into a $CaCl_2$ 0.1 M solution as mentioned above. Hexadecane was chosen because it is the solvent used by Crooks et al. (1990)[7] for the formation of MAA copolymer beads encapsulating cells, where it is harmless to cell viability. In this case, the emulsion was stabilized by the lecithin, while the size and buoyancy of capsules was controlled by varying the corn oil:n-hexadecane ratio. Higher proportions of corn oil produced small, buoyant capsules which did not precipitate into the aqueous phase, while higher proportions of hexadecane resulted in unstable emulsions which produced capsules of larger than cellular proportions (Table 2). The best results were obtained with a ratio of about 60% corn oil, 40% hexadecane. The emulsions for the dilution series experiment were formed using 10 mL solvent, 9 large drops of conidial solution, and 1 small drop of lecithin.

TABLE 2

Formation of capsules in various solvent ratios. In all ratios where capsules formed, conidial germination was ca. 100%. Ratios in bold font are desirable for encapsulation.

| Corn oil: n-hexadecane ratio | Capsule characteristics |
|---|---|
| 0:1 | Most >500 μm |
| 1:9 | Most >500 μm |
| 1:4 | Most >500 μm |
| 3:7 | Most >500 μm |
| 2:3 | Most <300 μm |
| 1:1 | Most <300 μm |
| 3:2 | Most <100 μm |

TABLE 2-continued

Formation of capsules in various solvent ratios. In all ratios where capsules formed, conidial germination was ca. 100%. Ratios in bold font are desirable for encapsulation.

| Corn oil: n-hexadecane ratio | Capsule characteristics |
|---|---|
| 7:3 | Most <200 μm |
| 4:1 | No yield |
| 9:1 | No yield |
| 1:0 | No yield |

Figure 2:
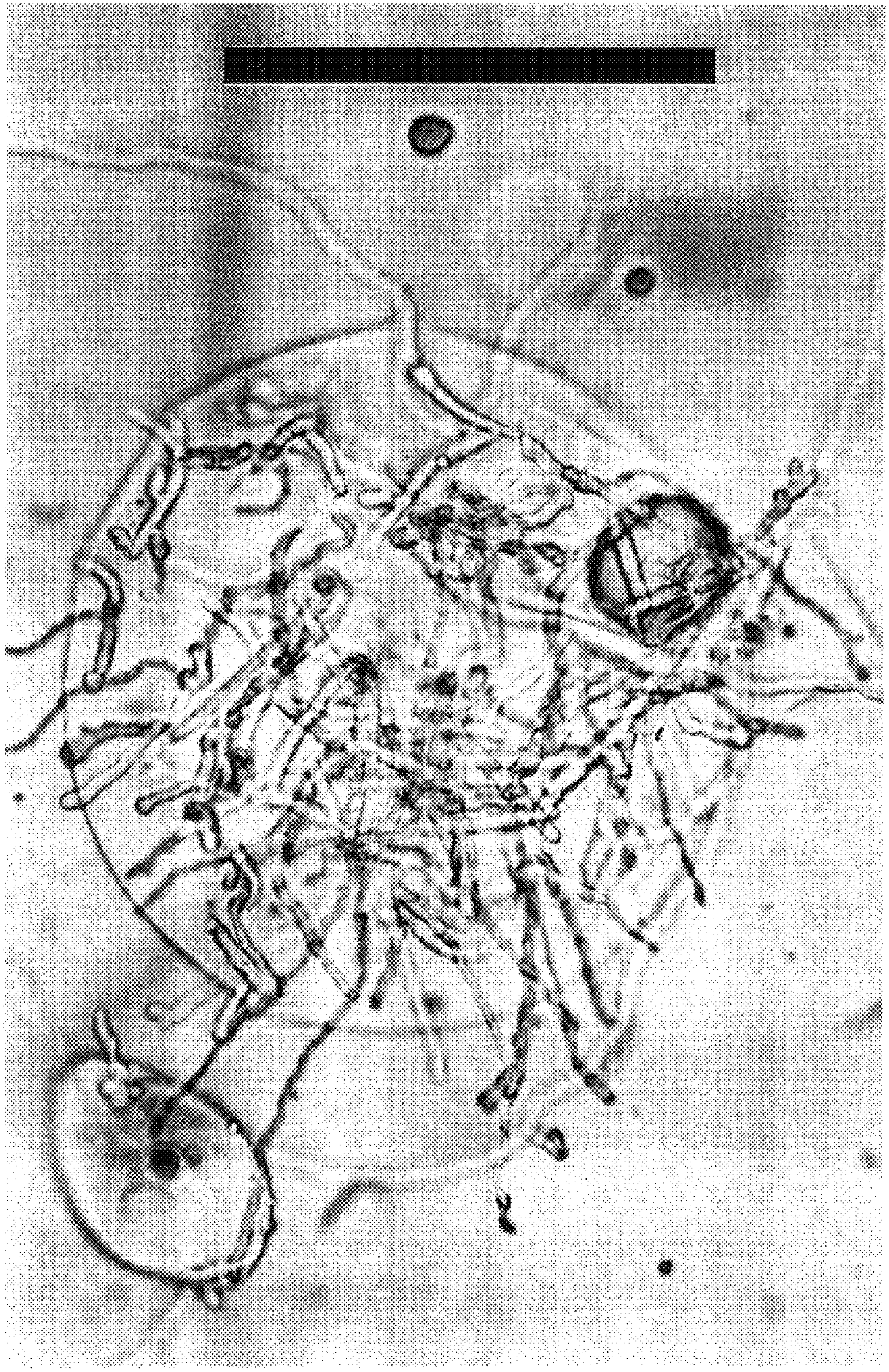
FIG. 2 is a photomicrograph of a similar capsule, with germinating conidia. The black scale bar is 100 μm long.

The capsules formed by this method can be very small (<100 μm diameter) (FIG. 1). Macroconidia (spores) of *Fusarium avenaceum* (another potential biocontrol agent of marsh reed grass, q.v. Winder 1997[6]) encapsulated by this method in alginate beads were viable and germinated at normal percentages, with germ tubes rupturing out of the capsules—exposure to hexadecane does not appear to inhibit spore germination (FIG. 2)

A further study (test tube assay) was done to more precisely determine the capsule size and encapsulation efficiency, as a result of various ratios of corn oil and n-hexadecane.

Figure 3:
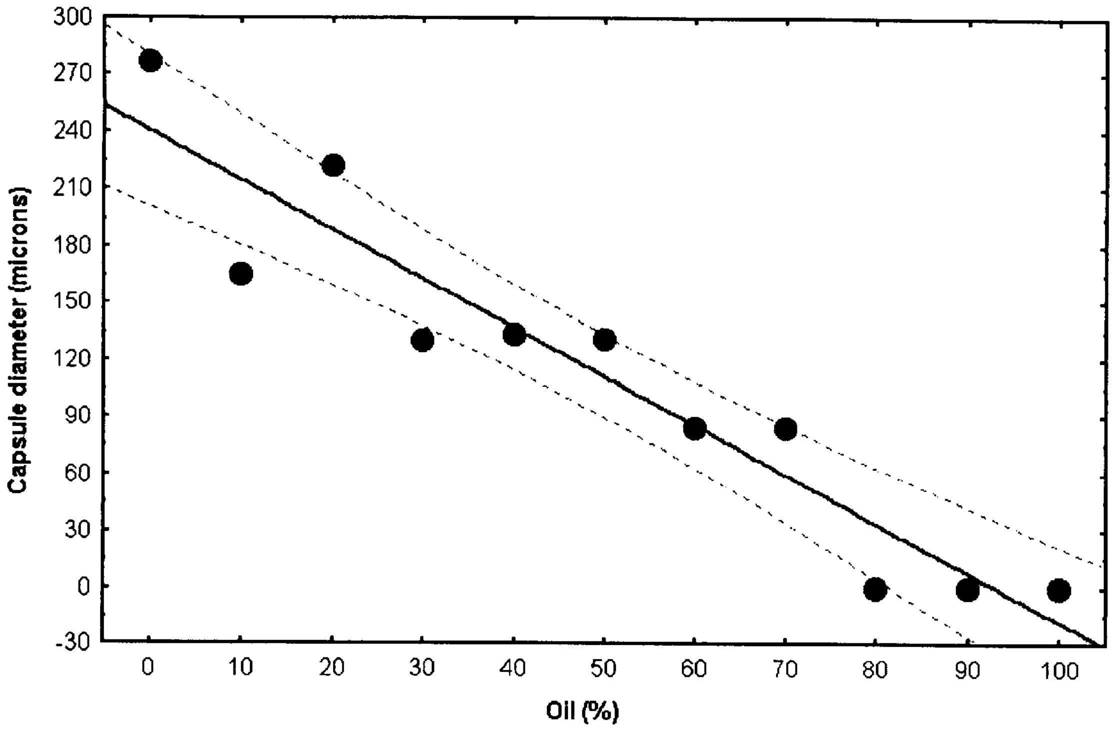
FIG. 3 is a graph illustrating the effect of dispersion medium composition on capsule diameter. The regression line shows a significant ($P<0.0001$) trend, and the dashed lines show 95% confidence limits for the trend.

Specifically, dispersion media consisting of 0, 10, 20, 30, 40, 50, 60, 70, 80, 90 and 100% corn oil versus n-hexadecane were prepared (each containing 0.1% lecithin). 10 mL of each medium were poured into a test tube (3 replications per medium type). The media were vortexed for 5 seconds with 10 drops of an aqueous 1% sodium alginate solution containing 1 mg/100 mL Evan's Blue dye for visualizing the precipitation. The resulting emulsions were layered over 5 mL of 0.01 M $CaCl_2$ solution and the diameter of the first 50 capsules harvested from each tube was measured with a microscope. Oil concentration of less than 50% tended to favor production of larger droplets in the emulsion, and fusion of the capsules into irregular masses as they precipitated. Higher oil concentrations favored smaller capsules (see FIG. 3). Oil concentrations greater than 70% did not allow for precipitation, and the alginate droplets were very small (<50 microns) and well mixed with the dispersion medium under those conditions. The addition of liquid soap to an 80% system induced a few capsules to precipitate, indicating that surface tension at the catalyst (polymerizing agent)/dispersion medium interface is partially responsible for regulating the occurrence of precipitation (the other factor is probably droplet size). This also means that any surface tension reducing surfactant could be added to the catalyst solution as part of any final method, as a way to reduce n-hexadecane consumption. Precipitation in the 70% systems was generally less rapid, and one 70% system did not form precipitate, indicating that 70% corn oil:n-hexadecane is very near the threshold beyond which precipitation will not occur, i.e. in the absence of any surfactants in the catalyst solution. Overall, we attribute the effect of oil concentration on droplet size to the combined effects of viscosity and specific gravity.

Figure 4:
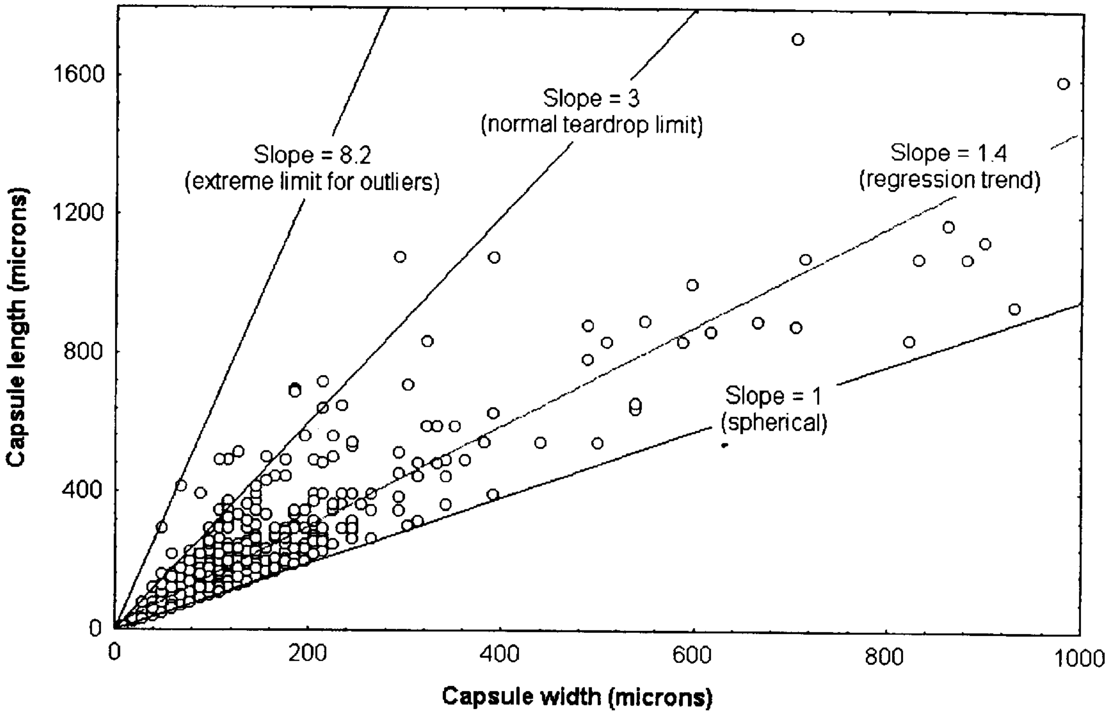
FIG. 4 is a graph illustrating the relationship between capsule diameter and capsule length. The regression line shows a significant ($P<0.0001$) trend.
Figure 5:
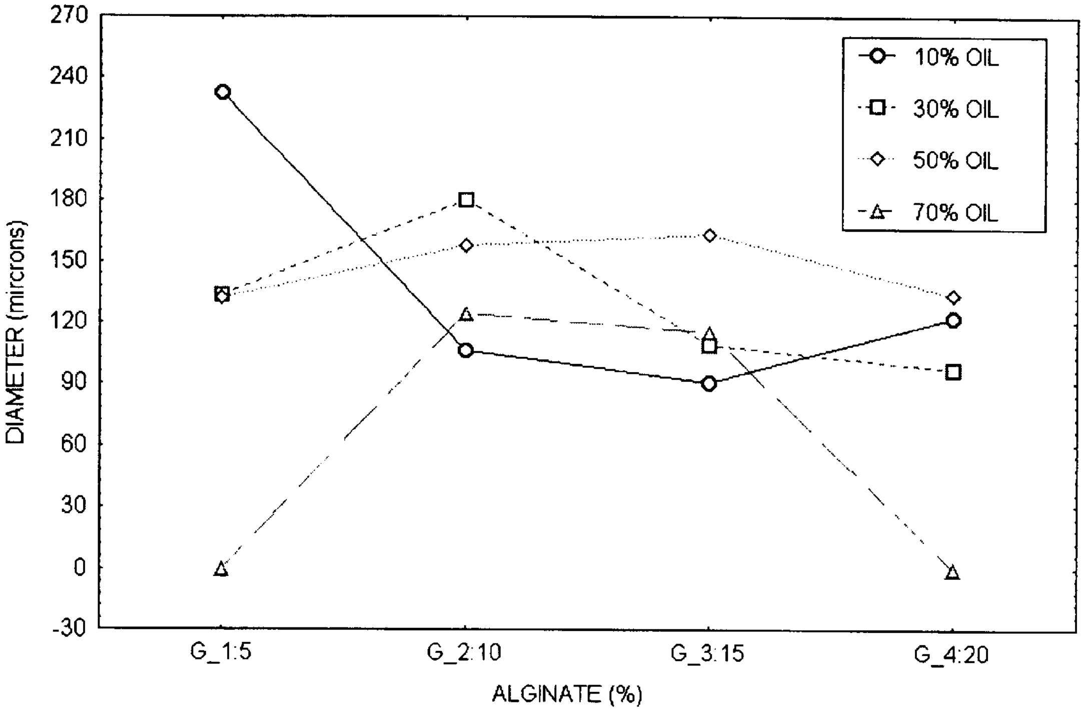
FIG. 5 is a graph illustrating the effects of dispersion medium composition (ratio of corn oil:n-hexadecane) and alginate concentration on the diameter of capsules produced by the corn oil method.
Figure 6:
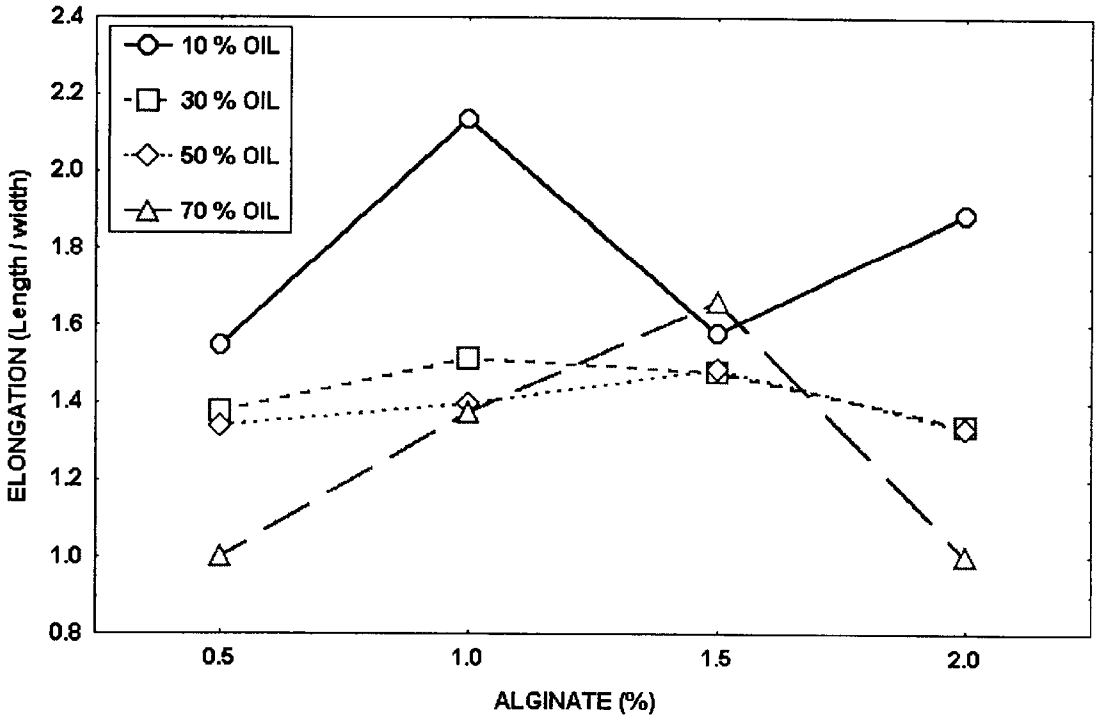
FIG. 6 is a graph illustrating the effects of dispersion medium composition (ratio of corn oil:n-hexadecane) and alginate concentration on the diameter and shape of capsules produced by the corn oil method. The ratio of capsule length:width is a measure of capsule elongation, with a value of 1 corresponding to a spherical shape, and higher values corresponding to elongation. Values of zero indicate that precipitation did not occur in the particular treatment combination.

A further factorial study (test tube assay) was done to more precisely determine capsule diameter and length in relation to the proportion of corn oil:n-hexadecane and the percentage of alginate in the precipitating droplets. Specifically, dispersion media consisting of 10, 30, 50, and 70% corn oil versus n-hexadecane were prepared (each containing 0.1% lecithin). Each medium was poured into separate test tubes (5 mL per tube). Aqueous solutions of 0.5%, 1%, 1.5%, and 2% aqueous sodium alginate were prepared, and for each solution, four drops were placed into a separate tube of each medium type, resulting in 16 combinations of medium type and alginate concentration. The media were vortexed for 5 seconds and the resulting emulsions were layered over 5 mL of 0.01 M $CaCl_2$ solution. The diameter and length of the first 14 capsules harvested from each tube was measured with a microscope. In general, capsule length tended to be about 40% longer than capsule diameter, with most capsules being less than 200% longer, and no capsules being more than 700% longer FIG. 4). Oil and alginate concentrations affected the size of emulsified globules (FIG. 5), with no precipitation occurring for high (70%) proportions of oil combined with high (2%) or low (0.5%) proportions of alginate. We attribute these results to the lower specific gravity of 0.5% alginate at one extreme, and the higher viscosity of 2% alginate at the other. In low (10%) proportions of oil combined with 1% alginate, the ratio of capsule length to width was significantly greater (FIG. 6). We attribute the elongation of these capsules to reduced surface tension at the interface between the dispersion medium and the aqueous catalyst solution, combined with a slightly larger capsule size and reduced capsule buoyancy. As surface tension is reduced, the larger globules were precipitating further into the aqueous catalyst solution before remnants of the dispersion medium retracted to allow polymerization. This resulted in elongation of the teardrop shape.

Figure 7:
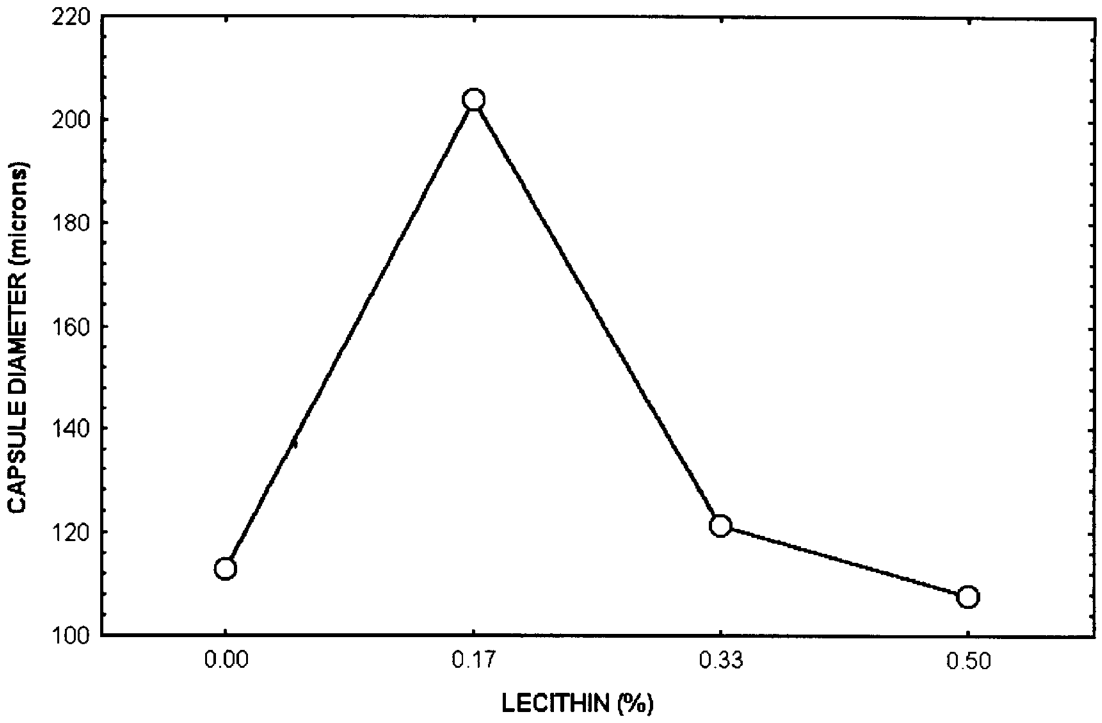
FIG. 7 is a graph illustrating the effects of emulsifier (lecithin) concentration on the diameter of capsules produced by the corn oil method.

A further study (test tube assay) was conducted to determine the effect of emulsifier (lecithin concentration) on capsule size and the efficiency of capsule production. 10 mL of a dispersion medium consisting of 1:1 corn oil:n-hexadecane was dispensed into test tubes, and lecithin was added to make dispersion media containing either 0, 0.17, 0.33, or 0.50% lecithin. For each type of dispersion medium, there were three replications. 9 drops of an aqueous solution of 1% sodium alginate were added to each tube and vortexed. Capsules were generated by layering the medium over an aqueous solution of 0.01M $CaCl_2$, and capsule diameters and lengths were measured as previously described. Increasing proportions of lecithin controlled capsule size by stabilizing the emulsion, thus preventing fusion of globules and allowing smaller capsules to precipitate (FIG. 7). Although a few capsules formed in the absence of lecithin (FIG. 7), production was almost nil, since most of the alginate fused at the interface between the dispersion medium and the aqueous catalyst solution. It is therefore necessary for an emulsifier to be present if substantial numbers of individual capsules are to be formed. With a small (0.17%) amount of lecithin, a moderate amount of capsules were produced. With greater proportions of lecithin, the efficiency of production increased to include nearly all of the alginate. It is evident that proportions of lecithin greater than 0.17% are desirable for obtaining maximum stability of the emulsion and therefore efficiency of production (FIG. 7). The proportion of lecithin had no significant effect on the capsule length:width ratio.

We expect that the actual upper limit is the amount that would begin to significantly increase viscosity or alter the specific gravity or surface tension of the dispersion medium. The precise achievable limit would be relative to other factors. Certainly, 100% lecithin would be more of a paste than a liquid, and precipitation would not occur. The actual upper limit would depend greatly on the proportion of oil in the dispersion medium and the quality (purity, type) of lecithin.

A further study (test tube assay) was performed to determine the effect of catalyst ($CaCl_2$) concentration on capsule shape and production efficiency. A dispersion medium consisting of 1:1 corn oil:n-hexadecane was prepared, containing 0.2% lecithin. 5 mL of the dispersion medium was dispensed into six separate test tubes, and 4 drops of 1% aqueous solution of sodium alginate were added to each tube. Tubes were vortexed as previously described and for each tube the dispersion medium was layered over either a 0.01 M or 1.0 M aqueous solution of $CaCl_2$ (three tubes per $CaCl_2$ concentration). Capsule lengths and widths were measured as previously described. The higher concentration of catalyst nearly halved capsule diameter, from 158±19 μm in 1.0 M $CaCl_2$ to 85±6 μm in 0.01 M $CaCl_2$. Efficiency was also nearly 100% and capsules were much less irregular in shape at the higher concentration of $CaCl_2$. We attribute these effects to changes in surface tension and rate of catalyst diffusion into the capsules. At higher concentrations of $CaCl_2$, surface tension of the aqueous catalyst solution is reduced, so that globules more readily precipitate across the interface with the dispersion medium and polymerize rapidly before they fuse with nearby globules. There was no significant effect of catalyst concentration on the length:width ratio of the capsules.

We expect that the upper limit is the amount that would begin to either significantly increase viscosity or alter the specific gravity of the catalyst solution, or the amount which would begin to significantly reduce the viability or activity of encapsulated cells. Again, the precise achievable limit will also depend on the type of dispersion medium, and the type of cells that are encapsulated.

It will be appreciated that the encapsulated materials may include crystals, liquid droplets, gas bubbles, other capsules, or other microparticles with chemical, electrical, or physical activity.

Moreover a wide variety of substances can be included with the encapsulted material. In many types of formulations it is usual to include substances which may affect the biological or physical performance of the encapsulated material (see the Green et al., 1998[2]. Some general classes of substances that could be used to affect the behavior, appearance, or taste of encapsulated biomaterials are nutrients, preservatives, buffers, growth factors, toxins, enzymes, flavors, odors, pigments, dyes, chemical signals, adhesives, and gases. In biological control, it may be very advantageous to encapsulate the above kinds of substances along with biomaterials, because the materials would remain concentrated in the capsule even after dissemination into the environment.

Protective qualities

Figures 8, 9:
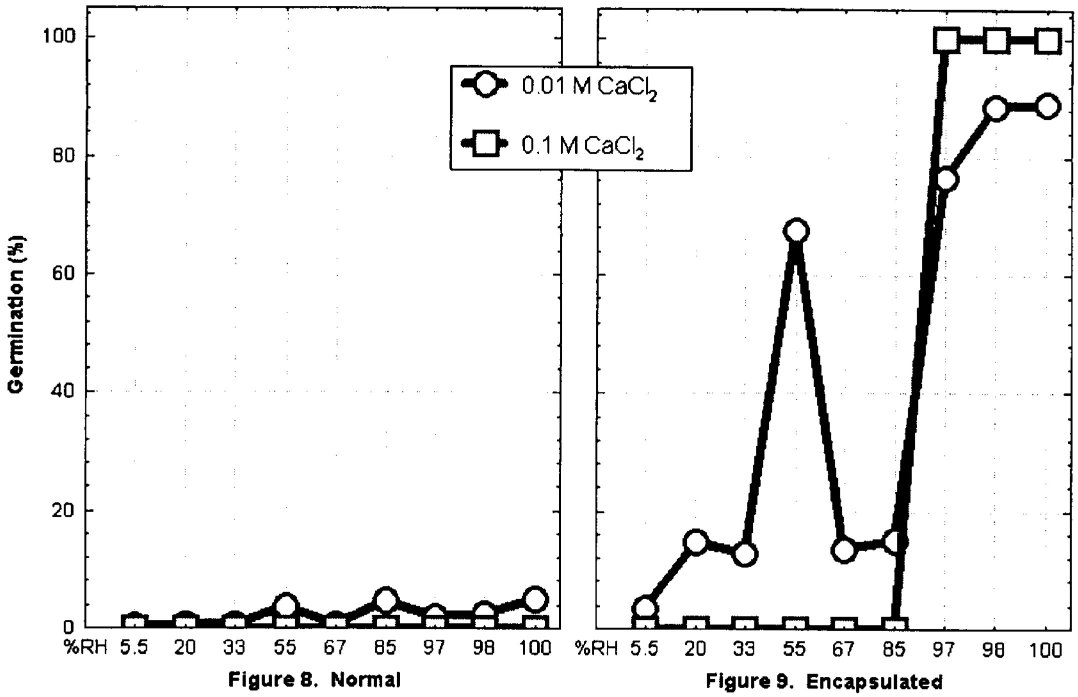
FIGS. 8 and 9 are graphs illustrating the effects of relative humidity and $CaCl_2$ concentration on the germination of plain (control), or encapsulated conidia of *Fusarium avenaceum,* respectively.
Figure 10:
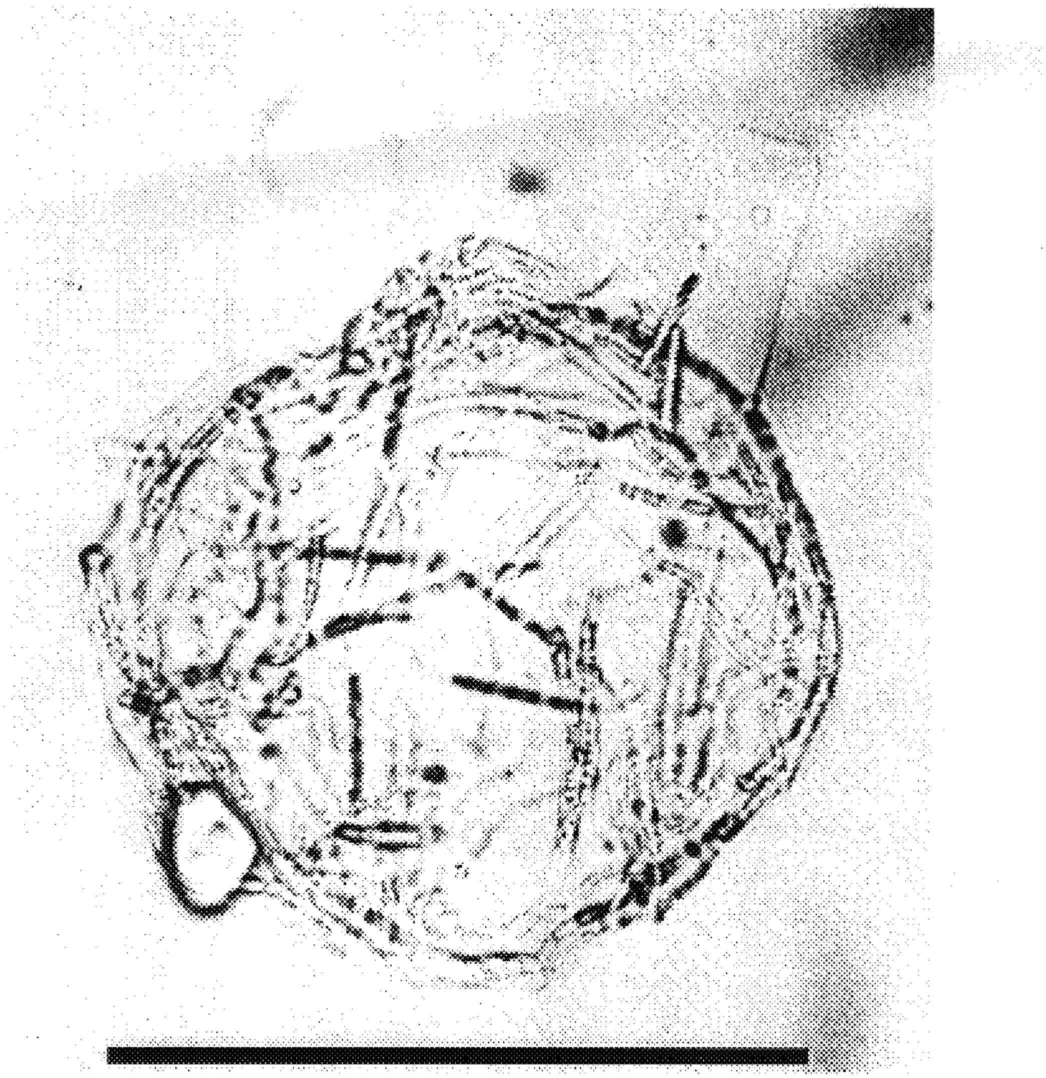
FIG. 10 is a photomicrograph of a capsule generated by the corn oil method, with conidia of *Fusarium avenaceum* germinating in 20% relative humidity, illustrating that the germ tubes remain inside the capsule until conditions are more favorable. The black scale bar is 100 μm long.

As research on this encapsulation method progresses, amendment to the corn oil method outlined above may become necessary as we discover ways to improve the capsule design and resistance of inoculum to desiccation. However, we already see evidence that the capsules will provide some protection from desiccation, in conjunction with the presence of $CaCl_2$ in the inoculum solution. We have assayed the germination of encapsulated macroconidia of *F. avenaceum* at 20° C. in drops placed a range of small glass humidity chambers. The relative humidity (RH) in the small glass chambers was controlled according to the method of Winston and Bates (1960)[8], the disclosure of which is incorporated herein by reference, with saturated chemical solutions, which produce a partial pressure of water vapor in a sealed space which is readily calculable. There were four replications (separate drops) per humidity value per trial—statistically significant ($P<0.001$) effects are summarized as follows. Conidia were encapsulated as in the corn oil method above. Encapsulated conidia in 0.1 M $CaCl_2$ germinated readily at higher RH values, but lost viability at 85% RH. We attribute this to greatly increased concentrations of $CaCl_2$ at lower RH values as the drops evaporated. *F. avenaceum* conidia did not germinate in pure water. We attribute the better germination in capsules to the presence of nutrients in the alginate, and the osmotic effect of the $CaCl_2$ (FIGS. 8 and 9). When we encapsulated the conidia using 0.01 M $CaCl_2$, a different picture emerged. The hygroscopic calcium salt allowed for a scant germination in controls at higher RH values, and maintained enough water film for a very few conidia to germinate even in the driest conditions. This was not unexpected, since evaporation was not instantaneous and various salts are known to stimulate germination of spores in many fungal species. This does not, therefore, limit the scope of the invention. Germination was much greater for encapsulated conidia, where conidia germinated in substantial numbers even under fairly dry conditions. A peak occurred at 55% RH, which we attribute to differences in the hygroscopic properties of the partially evaporated droplets. Below 55% RH, germ tubes remained inside the capsules (FIG. 10). These results demonstrated the potential for practical uses of the method.

Case 3

Figure 11:
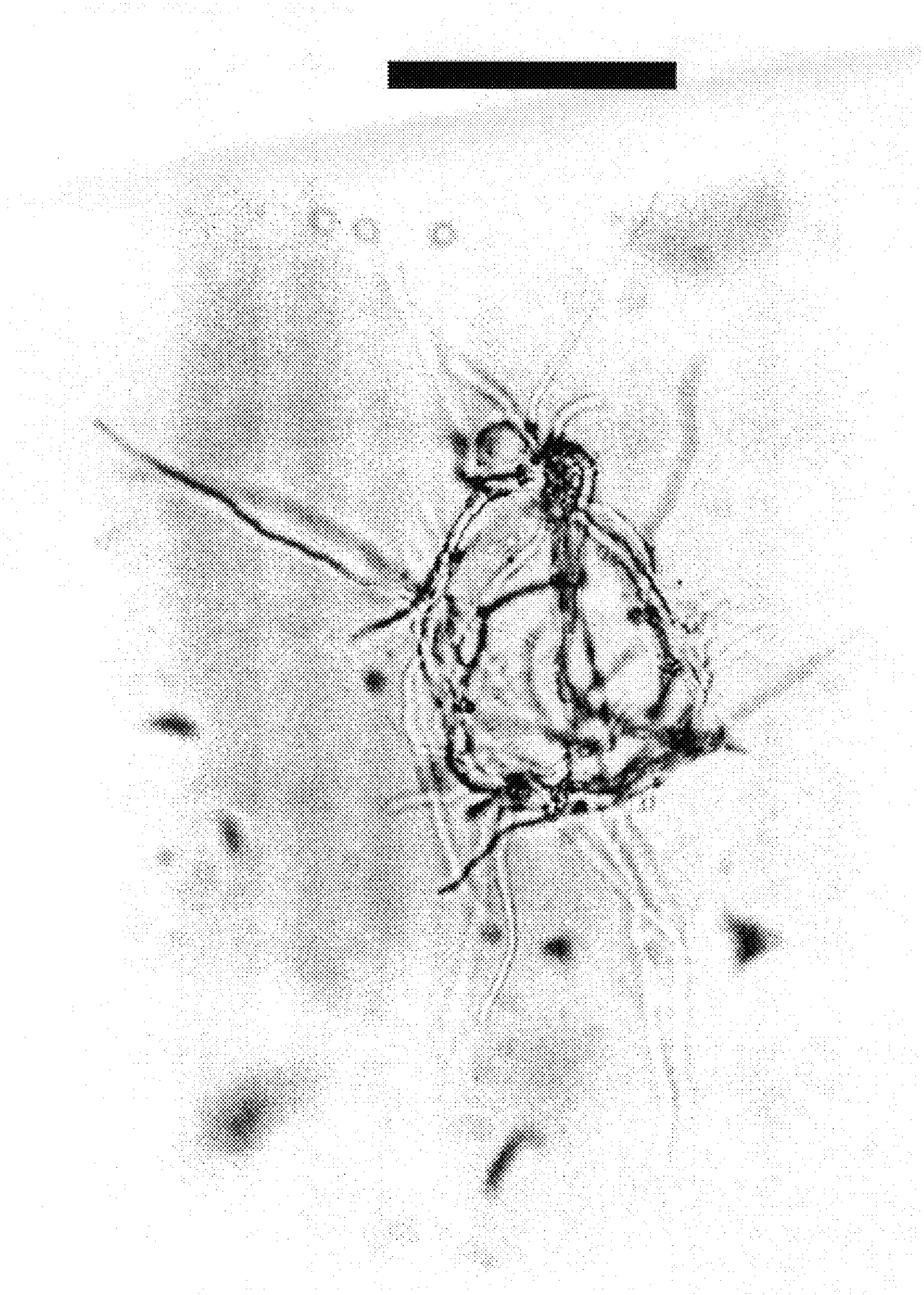
FIG. 11 is a photomicrograph of the hyphae of *Chondrostereum purpureum* (Pers. Ex Fr.) Pouzar encapsulated using the corn oil method, germinating on a microscope slide exposed to the air. The black scale bar is 100 μm long.

The corn oil method stated in case 2 above was used to engineer artificial microscopic spores of the fingus *Chondrostereum purpureum.* The dispersion medium consisted of a 6:4 ratio of corn oil:n-hexadecane, with 0.2% lecithin as an emulsifier. Hyphal clumps of *Chondrostereum purpureum* were produced in a liquid malt extract culture using standard microbiological methods. 10 mL of the culture was mixed with 100 mL of 1.0% sodium alginate, and 9 drops of the resulting suspension were added to 10 mL of the dispersion medium in a test tube. The tube was vortexed for 20 seconds, and the medium was layered over 10 mL of 1.0 M $CaCl_2$. Drops containing the resulting capsules were placed on microscope slides exposed to the air and examined for viability after 24 h. FIG. 11 shows hyphae of *Chondrostereum purpureum* germinating from one such capsule (all hyphae were internal to capsules prior to incubation). This result is significant in two respects. First, the hyphae of *C. purpureum* in liquid culture are thin-walled and fragile. In effect, our novel encapsulation technique has made a small clump of fragile hyphae into a robust spore. This may very well be the first instance of a deliberately engineered microscopic fungal spore. The other significance is that *C. purpureum* is being commercially developed as a biocontrol agent (see our commonly assigned U.S. Pat. No. 5,587,158). Moreover, it is difficult to spray existing hyphal formulations. Keeping in mind that spores of *C. purpureum* and many other types of fungi are difficult to mass-produce, we believe that this result demonstrates that we can make artificial spores for virtually any fungus, as long as we can grow the hyphae. Fungi that grow in artificial culture but do not produce useful quantities of durable spores include sterile deuteromycetes, biotrophic fungi, mychorrhizal mushrooms, and fungi which produce spores that are thin-walled and ephemeral. Using the above method, artificial spores could be produced for all of these types of fungi.

REFERENCES CITED

1. Auld, B. and Morin, L. 1995. Constraints in the development of bioherbicides. Weed Technology 9:638–652.
2. Green, S., Wade-Stewart, S., Boland, G., Teshler, M., and Liu, S. 1998. Formulating microorganisms for biological control of weeds. Pages 249–281 in Boland, G. and Kuykendall, L., Eds., Plant-microbe interactions and biological control. Marcel Dekker, Inc., N.Y.

3. Connick, W., Boyette, D., and McAlpine, J. 1991. Formulation of mycoherbicides using a pasta-like process. Biological Control 1:281–287.
4. Connick, W., Daigle, D., Quimby, P. 1991. An improved invert emulsion with high water retention for mycoherbicide delivery.
5. Nilsson K., Birnbaum S., Flygare S., Linse L., Schroder U., Jeppsson U., Larsson P.-O., Mosbach K. and Brodelius P. 1983 A general method for the immobilisation of cells with preserved viability. Eur. J. Appl. Microbiol. Biotechnol., 17:319–326.
6. Winder, R. 1997. The in vitro effect of allelopathy and various fungi on marsh reed grass (*Calamagrostis canadensis*). Canadian J. Botany 75:236–241.
7. Crooks, C A. Douglas, J A. Broughton, R. L., Sefton M V. (1990) Microencapsulation of mammallian cells in a hema MMA copolymer effects on capsule morphology and permeability. Journal of Biomedical Materials Research: 24(9):1241–1262
8. Winston P. and Bates, D. 1960. Saturated solutions for the control of humidity in biological research. Ecology 41: 232–237.

What is claimed is:

1. A method for encapsulation of microparticles in polymer matrix capsules having a diameter of about 10 μm to about 400 μm, comprising:

(i) providing an aqueous suspension of the microparticles and a polymer matrix precursor, (ii) adding a non-cytotoxic, hydrophobic dispersion medium containing an emulsifier, to form an aqueous dispersion, (iii) agitating vigorously to form a stable emulsion of individual microscopic globules containing a microparticle and the polymer matrix precursor suspended therein, and (iv) adding the stable emulsion to an aqueous solution containing a polymerizing agent, to polymerize and precipitate the globules, to form microparticles encapsulated in polymer matrix capsules having said diameter and being of a teardrop shape baying a length of 40–200% longer than its diameter, wherein precipitation of the globules is regulated by substantially matching the Specific Gravity of the hydrophobic dispersion medium and the aqueous suspension.

2. A method according to claim 1, wherein the dispersion medium contains an oil and an organic solvent that regulates precipitation of the globules by varying the viscosity and specific gravity of the dispersion medium, and consequently varying globule size.

3. A method according to claim 1, wherein the emulsifier is selected from the group consisting of lecithin, bilayer forming lipids, cholesterol and mixtures thereof.

4. A method according to claim 3, wherein the emulsifier is lecithin in an amount of 0.1 to 0.5%.

5. A method according to claim 3, wherein the polymerizing agent includes a calcium ion.

6. A method according to claim 5, wherein the polymer matrix precursor is a non-cytotoxic polymer selected from the group consisting of alginate, polysaccharides, polylysine, starch and mixtures thereof.

7. A method according to claim 6, wherein the polymer matrix precursor is an alginate.

8. A method according to claim 1, wherein the dispersion medium comprises a hydrophobic solvent or mixture of solvents having a Specific Gravity of about 1.

9. A method according to claim 8, wherein the dispersion medium is a 1:3 mixture of chloroform:hexane.

10. A method according to claim 9, wherein the polymerizing agent is $CaCl_2$, at a concentration of 0.01 M to 1.0 M.

11. A method according to claim 2, wherein the dispersion medium comprises an oil and an organic solvent miscible with oil.

12. A method according to claim 11, wherein the polymerizing agent is $CaCl_2$ at a concentration of 0.01 M to 1.0 M, and wherein the emulsifier is lecithin at a concentration of 0.17 to 0.5%/v.

13. A method according to claim 12, wherein the oil is corn oil and the organic solvent is n-hexadecane, and wherein the polymer matrix precursor is an alginate.

14. A method according to claim 13, wherein capsule volume, diameter and length are controlled by adjusting the proportion of n-hexadecane, thus varying the viscosity and specific gravity of the dispersion medium, with the ratio of corn oil to n-hexadecane being in a range of about 2:3 to about 7:3.

15. A method according to claim 13, wherein capsule volume, diameter and length are controlled by adjusting the proportion of alginate, thus varying the viscosity of the suspended alginate phase, the alginate being in the form of a 1% aqueous solution.

16. A method according to claim 14, wherein the ratio is 3:2.

17. A method according to claim 1, wherein the microparticle is a viable cellular biomaterial and wherein the polymer-encapsulated biomaterial so formed retains its viability.

18. A method according to claim 17, wherein the cellular biomaterial comprises a fungal propagule.

19. A method according to claim 18, wherein the fungal propagules are conidia, spores or hyphal cells.

20. A polymer encapsulated microparticle, comprising a microparticle or microparticles encapsulated in a polymer matrix capsule, the polymer forming the polymer matrix being biodegradable, non-cytotoxic and water dispersible, the capsule being of a teardrop shape 10–400 μm in diameter and having a length of 40–200% longer than its diameter.

21. A polymer encapsulated microparticle according to claim 20, wherein the polymer is an alginate.

22. A polymer encapsulated microparticle according to claim 21, wherein the microparticle is a viable cellular biomaterial, whose viability is maintained after encapsulation.

23. A polymer encapsulated microparticle according to claim 22, wherein the biomaterial comprises a fungal propagule selected from the group consisting of conidia, spores and hyphal cells.

24. A polymer encapsulated microparticle according to claim 20, wherein the polymer matrtix is formed of a polymer selected from the group consisting of alginate, polysaccharide, polylysine, starch and mixtures thereof.

25. A herbicidal composition comprising the encapsulated microparticle of claim 20, wherein the microparticle is a viable propagule of a weed pathogenic fungus.

* * * * *